April 18, 1961 L. B. SHERRILL Plant Pat. 2,048
PEACH TREE
Filed July 12, 1960
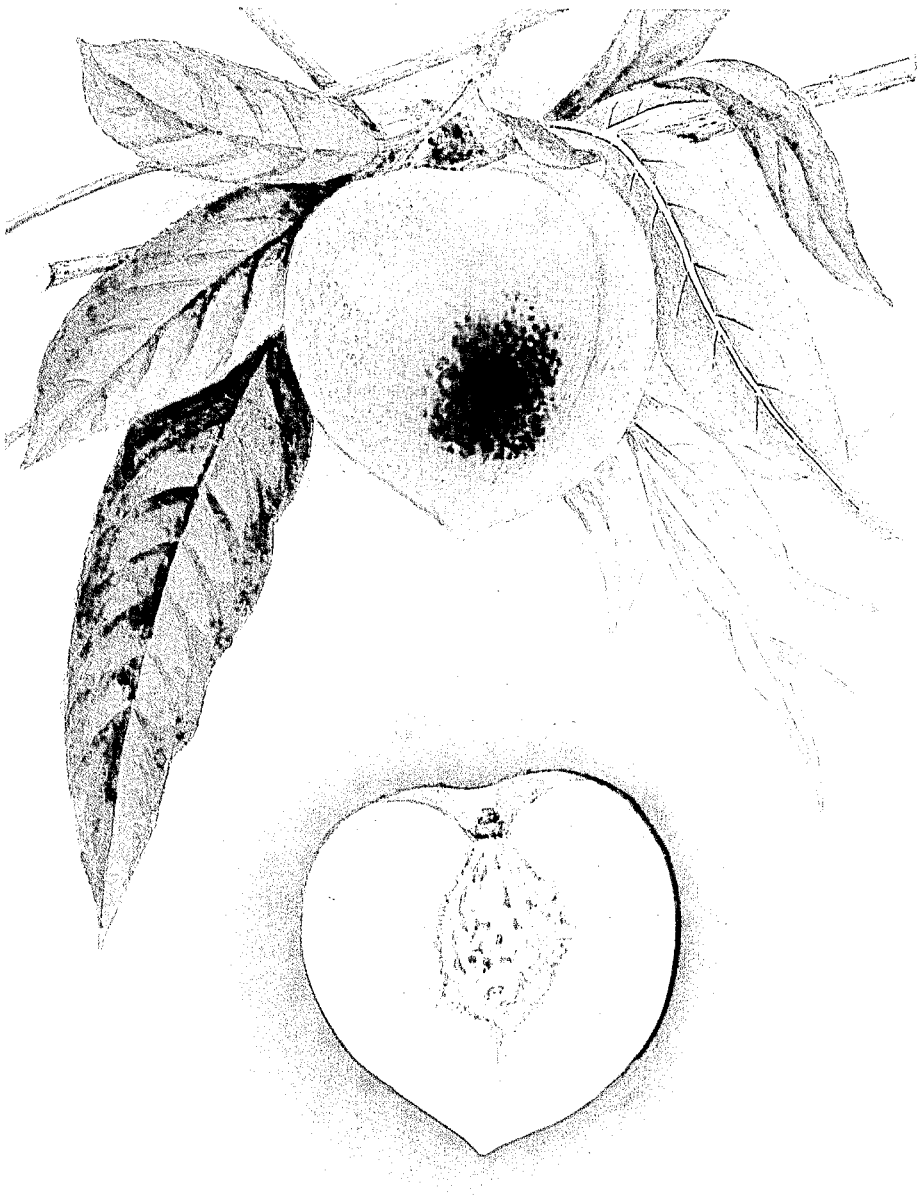
WITNESS
Addison E. Avery
INVENTOR
Lewis B. Sherrill
Webster & Webster
ATTYS.

United States Patent Office

Plant Pat. 2,048
Patented Apr. 18, 1961

2,048

PEACH TREE

Lewis B. Sherrill, Bakersfield, Calif., assignor of seventy-five percent to Patterson & Hale, Bakersfield, Calif., a partnership Filed July 12, 1960, Ser. No. 42,455

1 Claim. (Cl. 47—62)

This discovery relates to a new and distinct variety of peach tree which bears exteriorly red colored, substantially white fleshed, clingstone fruit, which—for the type—is relatively large; the variety having general resemblance to the Springtime peach (United States Plant Patent No. 1,268) and the Robin peach (United States Plant Patent No. 529), but has certain novel and advantageous characteristics.

In comparison with such prior varieties, the herein claimed variety of peach tree—while similar to the Springtime peach in appearance (medium size) and growing habit (vigorous) bears fruit which, throughout the entire growing season, is globose and very uniform and thus more nearly resembles the fruit of the Robin peach.

In further comparison, the fruit of the present variety has higher red exterior color, firmer flesh, a more acid flavor, and less split pits and resultant misshapes than the Springtime peach.

In still further comparison, the fruit of the present variety is in harvest approximately six days later than the Springtime peach, approximately seven days earlier than the Robin peach, and is substantially larger in size than either thereof.

The origin of the instant variety of peach tree is unknown, but is believed to be a sport of the Springtime peach; the parent tree having been discovered by me in a block of Springtime peaches growing in an orchard located in the Mettler Station area, Kern County, California. Such orchard is under my supervision, and when the parent tree bore fruit, the large size and higher exterior red color thereof attracted my attention. Upon comparative inspection it was apparent that the variety was quite distinct from both the Springtime and Robin peaches in the respects already described.

Subsequent to my discovery of the variety I asexually reproduced it—in the aforesaid orchard—by budding over a block of nectarine trees which were in the third leaf; dormant bud cut from the parent tree having been used for the purpose. Such reproductions, now in bearing, ran true to the parent in all respects.

In the drawings:

Fig. 1 is an elevation of one of the fruit, together with twigs and leaves.

Fig. 2 is a sectional elevation of one of the fruit, with the stone remaining in place.

Referring now more specifically to the pomological details of this new and distinct variety of peach tree, the following is an outline description thereof; all major color plate identifications being by reference to Maerz and Paul Dictionary of Color, except where otherwise indicated or where common terms of color definition are employed:

Tree:
- *Size.*—Medium.
- *Vigor.*—Vigorous.
- *Form.*—Upright; open; vase formed.
- *Hardiness.*—Hardy.
- *Production.*—Medium.
- *Bearing.*—Regular bearer.

Trunk:
- *Size.*—Medium.
- *Bark.*—Medium.

Branches:
- *Size.*—Medium.
- *Bark.*—Medium.
- *Color.*—Brown.
- *Lenticels.*—Number—medium. Size—medium.

Leaves:
- *Size.*—Medium. Average length—4" to 6". Average width—1".
- *Form.*—Lanceolate; acutely pointed.
- *Thickness.*—Medium.
- *Surface.*—Smooth.
- *Color.*—Mature leaves: top side—medium to dark green (20–L–6 to 22–L–8); under side—medium green (21–I–6). Young leaves: light green (18–L–3 to 19–L–4).
- *Margin.*—Finely serrate.
- *Petiole.*—Medium length.
- *Glands.*—Average number—two or three. Opposite; small; globose; positioned at base of blade on petiole.
- *Stipules.*—None.

Flower buds:
- *Hardiness.*—Hardy.
- *Size.*—Medium.
- *Length.*—Medium.
- *Form.*—Conic; free.

Flowers:
- *Blooming period.*—Date of first bloom—February 18, 1960. Date of full bloom—March 8, 1960. Early as compared with other varieties.
- *Size.*—Medium.
- *Color.*—Salmon.

Fruit:
- *Maturity when described.*—Firm ripe—May 10, 1960.
- *Date of first picking.*—May 10, 1960.
- *Date of last picking.*—May 18, 1960.
- *Size.*—Large—for the type and harvest season; somewhat variable. Average diameter axially 2½". Average transversely in suture plane—3".
- *Form.*—Uniform; symmetrical; globose.
- *Suture.*—Distinct; shallow, with slight depression beyond pistil point.
- *Lips.*—Equal to unequal.
- *Cavity.*—Elongated in suture plane, with suture showing on both sides. Average depth—⅜". Average breadth—½".
- *Base.*—Rounded.
- *Apex.*—Prolonged.
- *Pistil point.*—Apical.

Skin:
- *Thickness.*—Medium.
- *Texture.*—Medium.
- *Tenacity.*—Tenacious to flesh.
- *Tendency to crack.*—None.
- *Down.*—Moderate; medium length.
- *Color.*—Yellow-buff (11–I–7) substantially overspread with red (3–J–11 shading to 4–L–11), speckled with red (3–K–12) shading to a dark brown red (48–L–1).

Flesh:
- *Amygdalin.*—Wanting.
- *Texture.*—Medium.
- *Fibers.*—Few.
- *Ripens.*—Even.
- *Flavor.*—Acid.
- *Aroma.*—Distinct.

Flesh—Continued

*Eating quality.*—Good.

*Color.*—Pale creamy white (Naples yellow—British Colour Council Horticultural Colour Chart, 403/3 to 403/2); the flesh, at certain points adjacent the skin, shading to a pale pink (Maerz and Paul Dictionary of Color, 1–E–1).

Stone:

*Type.*—Cling.

*Size.*—Medium. Average length—1¼". Average breadth—¾". Average thickness—¾".

*Form.*—Ovoid; cuneate toward apex.

*Base.*—Straight.

*Hilum.*—Oval.

*Apex.*—Acute.

*Sides.*—Equal.

*Surface.*—Regularly furrowed near base.

*Ridges.*—Rounded.

*Pits.*—Angular.

*Dorsal edge.*—Full, with broad groove.

*Tendency to split.*—Slight.

*Color.*—Oyster-white (10–B–1).

Use: Dessert.

Keeping quality: Good.

Shipping quality: Good.

The tree and its fruit herein described may vary in slight detail due to climatic and soil conditions under which the variety may be grown.

The following is claimed:

A new and distinct variety of peach tree, as illustrated and described, which bears exteriorly red colored, substantially white fleshed, clingstone fruit of relatively large size; said variety, in comparison to the Springtime peach, being characterized by fruit which is in harvest approximately six days later, larger with higher red exterior color and firmer more acid flavored flesh, and less split pits, and, in comparison to the Robin peach, being characterized by fruit which is similarly globose and very uniform throughout the entire growing season but larger, and in harvest approximately seven days earlier.

No references cited.